United States Patent
Requardt

(10) Patent No.: US 6,397,097 B1
(45) Date of Patent: May 28, 2002

(54) METHOD AND CONTROL APPARATUS FOR TRACKING A CONTRAST AGENT IN AN EXAMINATION SUBJECT USING A MEDICAL IMAGING DEVICE

(75) Inventor: Martin Requardt, Nürnberg (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 09/268,776

(22) Filed: Mar. 16, 1999

(30) Foreign Application Priority Data

Mar. 16, 1998 (DE) .......................... 198 11 349

(51) Int. Cl.⁷ .............................. A61B 5/00
(52) U.S. Cl. .......................... 600/431; 600/420
(58) Field of Search ................. 600/410, 413, 600/419, 420, 431; 324/306, 309; 378/4

(56) References Cited

U.S. PATENT DOCUMENTS

| | | | |
|---|---|---|---|
| 5,417,231 A | | 5/1995 | Prince |
| 5,553,619 A | | 9/1996 | Prince |
| 5,579,767 A | | 12/1996 | Prince |
| 5,590,654 A | | 1/1997 | Prince |
| 5,687,208 A | * | 11/1997 | Bae et al. |
| 5,924,987 A | * | 7/1999 | Meaney et al. |
| 5,928,148 A | * | 7/1999 | Wang et al. |
| 6,033,645 A | * | 3/2000 | Unger et al. |
| 6,073,042 A | * | 6/2000 | Simonetti |
| 6,195,579 B1 | * | 2/2001 | Carroll et al. .............. 600/420 |

* cited by examiner

Primary Examiner—Marvin M. Lateef
Assistant Examiner—Shawna J Shaw
(74) Attorney, Agent, or Firm—Schiff Hardin & Waite

(57) ABSTRACT

In a method and control apparatus for tracking a contrast agent using an imaging medical device a test bolus of a contrast agent is initially injected into an examination subject, followed by an injection of a main bolus at a time interval of $\Delta t_i$. The arrival of the test bolus in the observation volume is chronologically determined by periodically repeated survey measurements. An image data measurement is started at a time interval $\Delta t_m$ subsequent to the detection of the test bolus, this time interval $\Delta t_m$ being defined according to the prescribed time interval $\Delta t_i$.

13 Claims, 3 Drawing Sheets

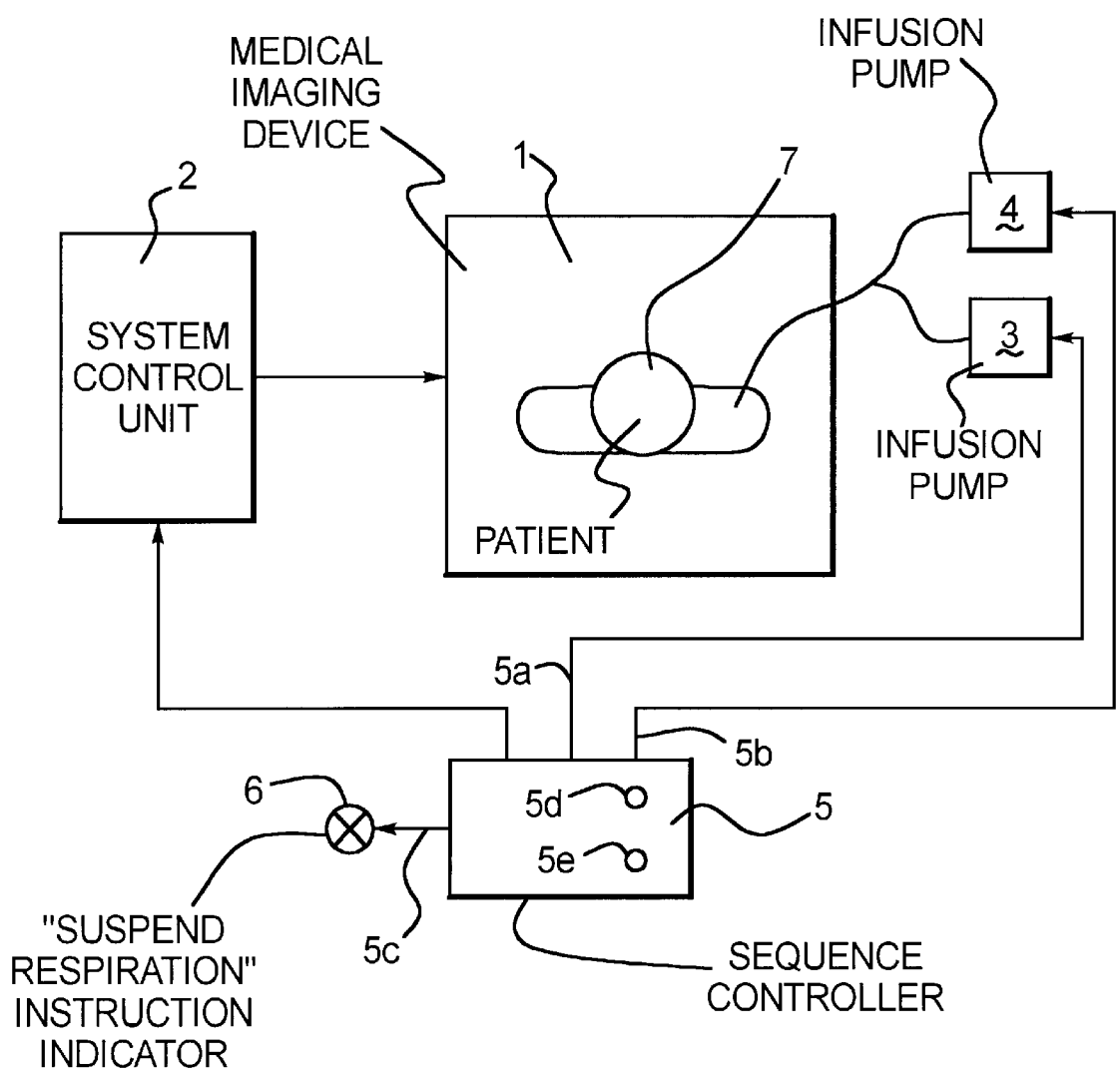

METHOD AND CONTROL APPARATUS FOR TRACKING A CONTRAST AGENT IN AN EXAMINATION SUBJECT USING A MEDICAL IMAGING DEVICE

BACKGROUND OF THE INVENTION

1. Field of the Invention

The present invention is directed to a method as well as to a control apparatus for tracking a contrast agent in an examination subject using a medical imaging device, such as a magnetic resonance imaging apparatus or a computed tomography apparatus, in which the examination subject is disposed.

2. Description of the Prior Art

In examinations involving a contrast agent, it is often required to trigger pickup at that time at which a previously injected volume of contrast agent reaches the examination volume of interest. The contrast agent is typically injected intravenously, and the examination is conducted as soon as the contrast agent is located in certain arteries. For example, in dynamic liver examinations, the liver is recorded during the arterial phase. There are different approaches with respect to this timing, according to the imaging method applied. In the increasingly popular MR angiography involving a contrast agent, care must be taken that at least the center of the k-space is recorded while the contrast agent concentration is high. The physical relations underlying this rule are detailed in U.S. Pat. Nos. 5,417,213; 5,553,619; 5,579,767 and 5,590,654, for example. Of course, for this approach an exact timing becomes more important as the duration of the increased contrast agent concentration becomes shorter relative to the total measuring time for the image acquisition.

In many angiography examinations, particularly in the abdominal region, the image data measurement must ensue in a period of arrested breathing, in order to avoid image artifacts due to respiratory motion. In such examinations, the patient is given the instruction to hold his or her breath prior to the beginning of the measurement. Of course, to make this possible it is necessary to know the starting time of the contrast agent enrichment, and also of the beginning of the image data measurement, in advance.

Previously, this problem was addressed by two different approaches. The timespan between injection and arrival of the contrast agent in a relevant examination volume can be separately determined. To this end, it suffices to inject a very small amount of contrast agent into the patient and to determine the arrival of the contrast agent in the relevant examination region by an imaging method. The time between a injection and arrival, which is termed the circulation time, is measured. The actual examination is then conducted with a normal amount of contrast agent, it being known on the basis of the previously determined circulation time when the image data measuring is to be started. With this knowledge, an instruction for the patient to arrest breathing can be given at the proper time prior to the image data acquisition.

Another method for MR angiography is described in U.S. Pat. No. 5,590,654. In this method data acquisition from the imaging volume is already started prior to the injection of a contrast agent. Subsequent to the injection of the contrast agent, further measurements are performed continually or periodically until the arrival of the contrast agent in the relevant examination region is established on the basis of changes relative to test measurements conducted without contrast agent. The actual image data acquisition is subsequently started. This method only requires an injection with a normal dose, however, with this method a time problem results in MR angiography, particularly if the image data measurement must be performed in an arrested-breathing phase. Low contrast agent volumes (e.g. 10 to 20 ml) are usually used in MR angiography. Given typical injection rates of 2 ml/s, the contrast agent bolus in the blood has a duration of 8 to 15 seconds. Since the instruction to suspend respiration can be given only when the imaging device has reported the arrival of the bolus in the relevant examination region, approximately 4 to 6 seconds of the total available measuring time of 8 to 15 seconds are lost, while the patient acts on the instruction to suspend respiration is converted into action. The remaining measuring time may already be too short for MR angiography. One solution would be to increase the contrast agent volume, in order to extend the available measuring time, however, due to possible side effects and also due to cost, it is desirable to keep the contrast agent volume small.

SUMMARY OF THE INVENTION

It is an object of the present invention to provide a method of the type described above wherein a low volume of contrast agent suffices and wherein image data acquisition can be chronologically synchronized, with optimal precision, with the arrival of a contrast agent bolus in the relevant examination region.

This object is inventively achieved in a method and control apparatus for tracking a contrast agent in an examination subject using a medical imaging apparatus allowing viewing of a relevant observation volume of the examination subject, wherein a test bolus of contrast agent is injected followed by injection of a liquid which is free of contrast agent, followed by the injection of a main bolus of contrast agent at a predetermined time interval $\Delta ti$ following the injection of the test bolus. The arrival of the test bolus in the observation volume is determined by periodically obtaining survey images of the relevant observation volume of the subject using the medical imaging apparatus. Subsequent to detection of the arrival of the test bolus, acquisition of imaging data is started at a time interval $\Delta tm$, with $\Delta tm$ being defined according to the predetermined time interval $\Delta ti$.

By means of the two-stage injection of the contrast agent at a precisely defined interval, a precise time for the optimal start of the image data acquisition, and also for the instruction, if needed, to suspend respiration, is obtained. Since the available measuring time can be used optimally, a small volume of contrast agent suffices. In an embodiment of the method, image data acquisition is automatically started at the predetermined time interval subsequent to the arrival of the test bolus. While the known methods require a considerable degree of attention from the examining doctor, particularly if an instruction to suspend breathing is necessary, the inventive method can be conducted entirely automatically. This reduces the error rate considerably. With a control apparatus and two infusion pumps, the contrast agent injection can also be automated.

DESCRIPTION OF THE DRAWINGS

FIG. 3 is a schematic illustration a device for practicing the inventive method.

DESCRIPTION OF THE PREFERRED EMBODIMENTS

The inventive method is described below in the context of a nuclear spin tomography examination (also referred to as MR, for magnetic resonance) which is supported by a contrast agent. The method, however, can also be analogously applied to other imaging modalities, such as computed tomography; it is usually necessary to use larger contrast agent volumes in computed tomography.

Figure 1:
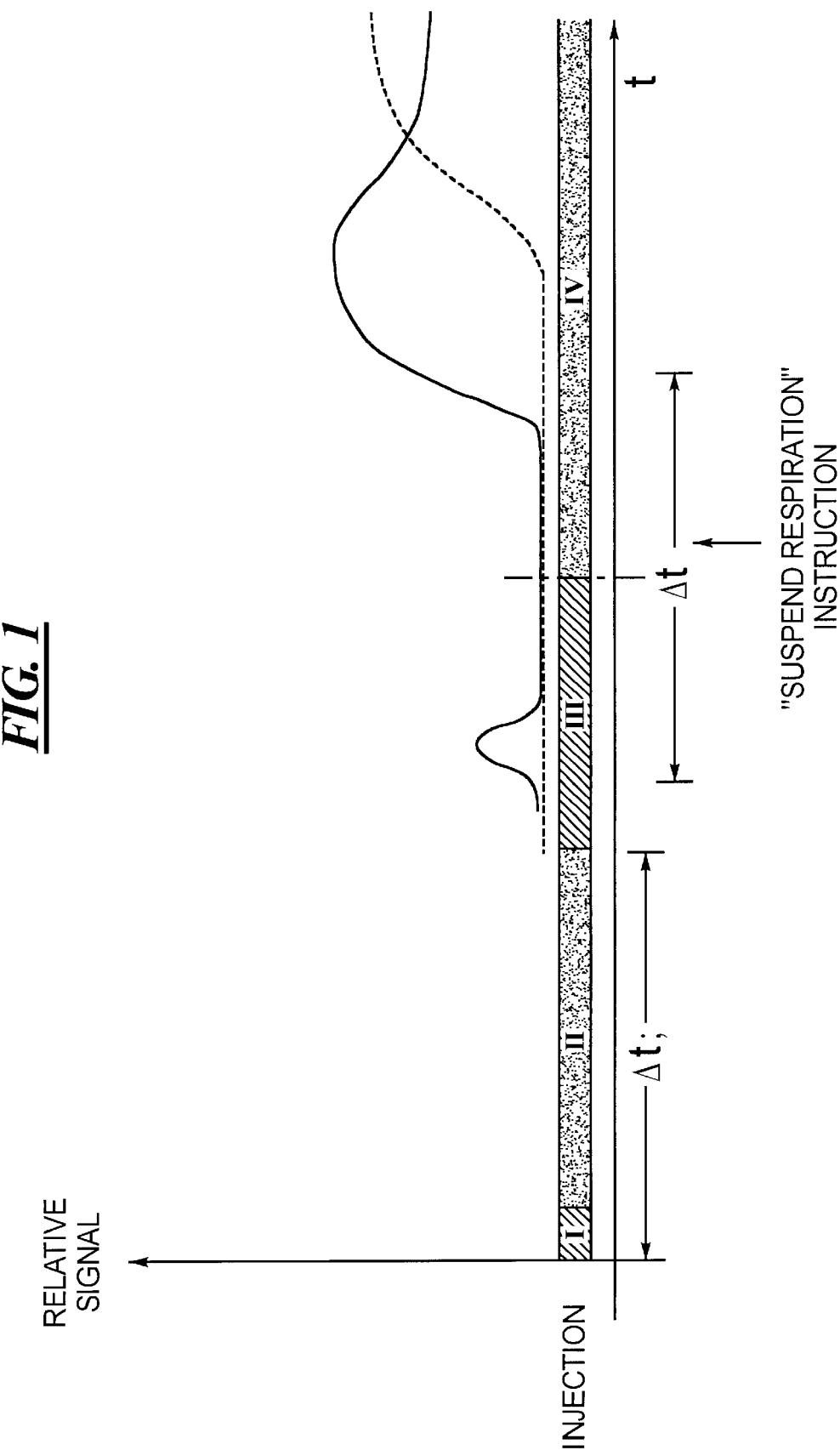
FIG. 1 illustrates the time sequence of the injection and the signal.

According to FIG. 1, a test bolus of about 1 ml is injected in a time period 1, which is illustrated in hatched fashion. For MR measurements, a paramagnetic contrast agent is required, such as is commercially available from Schering under the name Magnevist®. The injection of the test bolus is followed by the injection of a saline solution (characterized by a dotted surface) in a phase II and this is in turn followed by another contrast agent injection at a full dose in a phase III, i.e. the main bolus. The duration of the injection of saline solution in phase II determines the interval between the test bolus and the main bolus. The main bolus in phase III is followed by an injection of saline solution again in a phase IV. Approximately 15 ml of saline solution is typically injected in phases II and IV, respectively. Constant injection rates are preferably used, so that the injected volume is proportional to the time-span. An injection rate of 2 ml per second is typically used for MR examinations, so that, given a test bolus of 1 ml, phase I lasts ½ second, given an injection of 1 ml contrast agent; phase II lasts about 8 s, given an injection of 15 ml saline solution; and phase III lasts between 5 and 10 s given an injection of 10 to 20 ml contrast agent. The injection appropriately occurs with infusion pumps, as is also described in the above referenced patents.

Figure 2:
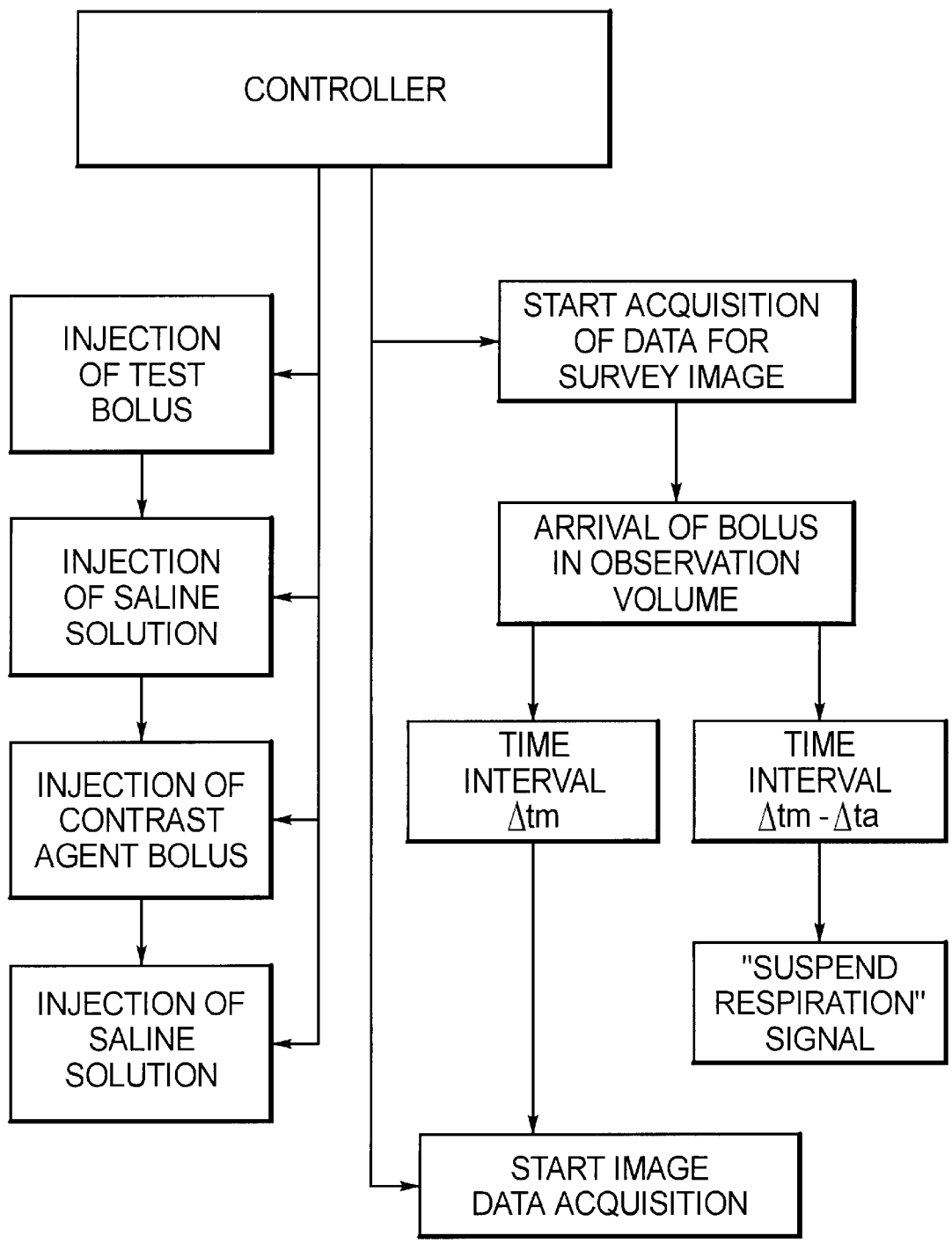
FIG. 2 is a flow chart of the inventive method.

As soon as the contrast agent has entered the examination volume, the nuclear resonance signal in that volume increases on the basis of the paramagnetic characteristics of the contrast agent. FIG. 1 illustrates the relative signal rise due to the contrast agent. In order to detect the arrival of the test bolus, nuclear resonance signals are obtained in a slice of the examination volume periodically, e.g. in a second cycle. Since, for this purpose, what is important is to detect a signal increase for this slice, a spatial resolution need not occur inside the slice; rather, it is sufficient to evaluate the total signal from the slice. This is particularly advantageous if the arrival of the test bolus is to be determined automatically on the basis of a signal change. Alternatively, an image from the slice with full or reduced resolution can be obtained and the MR technician can wait, with manual image control, for the arrival of the bolus in the examination volume. The time between the injection of the test bolus and the * arrival in the examination volume, i.e. the emergence of the first signal maximum according to FIG. 2, is between 13 and 25 s in the abdomen, for example. This time is also called the circulation time.

On the basis of the established time interval $\Delta ti$ between test bolus I and main bolus III, it is known that the main bolus must follow the arrival of the test bolus in the examination volume at the same time interval $\Delta ti$. This means that the signal maximum resulting from the main bolus must follow the signal maximum resulting from the test bolus in this time-span $\Delta ti$.

With this knowledge, corresponding actions can be carried out. For example, a breathing instruction can be given immediately prior to the acquisition of the main bolus, and then a pulse sequence can be started which acquires image data from the total relevant volume, given the emergence of the signal maximum for the main bolus. For reasons which are detailed in the above cited U.S. Pat. No. 5,417,213, it is advantageous for the image data from the center of the k-space to be obtained at the maximum of the signal rise due to the contrast agent infusion. Since the signal maximum for the main bolus can be very precisely predetermined with the method described herein, a precise timing for maintaining this condition is possible. In order to chronologically match the measuring of the central k-space times to the signal maximum on the basis of the enrichment of the contrast agent, it may be appropriate for the time interval $\Delta tm$ between the detection of the test bolus and the start of the image data measurement to be shifted in relation to the time interval $\Delta ti$ between the injection of test bolus and main bolus, the magnitude of the shift being determined experimentally.

As mentioned above, the measuring sequence can be controlled manually; i.e., the examining person observes the arrival of the bolus in a specific slice and triggers the measurement for the image data acquisition subsequent to the prescribed time $\Delta t$, possibly leaving a few seconds prior to this for an instruction to suspend respiration. The method can also be automated by a relatively simple control apparatus. An example of a suitable control sequence is schematically depicted in FIG. 2. According to the time scheme described in connection with FIG. 1, a sequence controller means controls a first infusion pump for a contrast agent solution and a second infusion pump for a saline solution. Furthermore, the survey measurement for the bolus arrival is also started via this time controller. As soon as a bolus arrives in the observation volume, preferably in a slice of the observation volume, the measurement for the image data acquisition is started, subsequent to the time interval $\Delta tm$ as prescribed by the time control. In a shorter time interval $\Delta tm - \Delta ta$ after the arrival of the observation volume, a "suspend respiration" signal is emitted to a message output.

With the described method, contrast agent examinations can be considerably shortened compared to conventional methods, and erroneous measurements can be reduced. On the basis of the precise timing, breathing instructions can be given with such chronological precision that error measurements due to movement can be reduced. Since the acquisition window for the measurement data acquisition can be exactly coordinated with the signal maximum, a low contrast agent volume suffices. This also holds true for CT examinations. The risk of complications is thus lower, and the consumption of expensive contrast agents is limited.

An overall system for practicing the method is schematically depicted in FIG. 3. The examined patient 7 lies in a medical imaging device 1, which can be a CT device or an MR device, for example. The patient 7 is connected to two infusion pumps 3 and 4 for a contrast agent solution and a saline solution, respectively. The medical examination device 1 is controlled by a system control unit 2. The infusion pumps 3 and 4 are controlled with a sequence controller 5 as described above. Furthermore, the survey measurement for the arrival of a bolus in a predetermined slice and the measurement for the imaging data acquisition are also started via the system controller 2. The sequence control apparatus 5 also receives a signal from the system controller 2 as soon as the test bolus has been detected. The sequence control apparatus 5 has a message output indicator 6 for a "suspend respiration" instruction. The injection volume of the injection pumps 3 and 4 can be prescribed by adjusting elements 5a and 5b. The sequence control apparatus 5 need not be constructed as a separate device as hardware, but can also be integrated into the system controller 2 as software. Compared to a conventional system controller, only two additional control outputs 3 and 4 are necessary for the control of the infusion pumps. The communication of the repiration instruction can be produced with existing system components, e.g. via a monitor. It is a particular advantage of this inventive method that it can be implemented in conventional systems with slight modifications.

Although modifications and changes may be suggested by those skilled in the it is the intention of the inventor to embody within the patent warranted hereon all changes and modifications as reasonably and properly come within the scope of his contribution to the art.

I claim as my invention:

1. A method for tracking a contrast agent in an examination subject, comprising the steps of:

disposing an examination subject in a medical imaging apparatus;

injecting a test bolus of a contrast agent into said examination subject;

subsequently injecting a liquid into said examination subject which is free of contrast agent;

subsequently injecting a main bolus of contrast agent into said examination subject at a predetermined time interval $\Delta ti$ following injection of said test bolus so that said test bolus, said liquid and said main bolus are injected in immediate succession;

monitoring an arrival of said test bolus within an observation volume of said examination subject by periodically and repeatedly obtaining survey images of said observation volume of said examination subject using said medical imaging apparatus; and subsequent to identifying the arrival of said test bolus in said observation volume, beginning data acquisition for a diagnostic image of said examination subject using said medical imaging apparatus for a time interval $\Delta tm$, and selecting $\Delta tm$ dependent on said predetermined time interval $\Delta ti$.

2. A method as claimed in claim 1 wherein the step of periodically and repeatedly obtaining said survey images comprises periodically and repeatedly obtaining survey images with a low spatial resolution.

3. A method as claimed in claim 2 wherein the step of periodically and repeatedly obtaining said survey images with a low spatial resolution comprises periodically and repeatedly obtaining said survey images with a spatial resolution in only one direction.

4. A method as claimed in claim 3 wherein said test bolus has a substantially smaller volume than said main bolus of contrast agent.

5. A method as claimed in claim 1 wherein the step of starting acquisition of data for said diagnostic image comprises automatically starting acquisition of data for said diagnostic image.

6. A method as claimed in claim 1 wherein the step of disposing said examination subject in a medical imaging apparatus comprises disposing said examination subject in a magnetic resonance imaging apparatus, and wherein the step of acquiring said data for said diagnostic image comprises acquiring frequency-coded and phase-coded nuclear resonance signals, and comprising the additional step of sorting said nuclear resonance signals into a k-space matrix ordered by respective phase factors of said nuclear resonant signals, and wherein the step of selecting said time $\Delta tm$ comprises selecting $\Delta tm$ so that a central region of k-space is measured while a maximum contrast agent concentration is present in said observation volume.

7. A method as claimed in claim 1 wherein the step of disposing an examination subject in a medical imaging apparatus comprises disposing said examination subject in a magnetic resonance imaging apparatus, and wherein the step of acquiring data for a diagnostic image comprises acquiring magnetic resonance imaging data for producing a magnetic resonance image.

8. A method as claimed in claim 1 wherein the step of disposing an examination subject in a medical imaging apparatus comprises disposing said examination subject in a computed tomography apparatus, and wherein the step of acquiring data for a diagnostic image comprises acquiring radiographic data for producing a computed tomographic image.

9. A method as claimed in claim 1 wherein said test bolus has a circulation time in said examination subject associated therewith, and wherein the step of subsequently injecting said main bolus of contrast agent comprises selecting said predetermined time interval $\Delta ti$ to be less than said circulation time.

10. In a medical imaging apparatus wherein image data are acquired and wherein a diagnostic image is produced from said image data, the improvement of a control apparatus for tracking a contrast agent in said examination subject comprising:

a first infusion pump adapted for connection to an examination subject for infusing a contrast agent into said examination subject;

a second infusion pump for infusing a liquid into said examination subject which is free of contrast agent;

a controller connected to said first infusion pump and to said second infusion pump, said controller operating said first infusion pump to inject a first contrast agent bolus into said examination subject followed at a predetermined time interval $\Delta ti$ by injection of a second contrast agent bolus into said examination subject, with an injection of said liquid which is free of contrast agent from said second infusion pump during said interval $\Delta ti$, so that said first contrast agent bolus, said liquid and said second contrast agent bolus are injected in immediate succession;

said controller having an input for receiving a status signal from said medical imaging apparatus indicating arrival of said first bolus of contrast agent in an examination volume; and said controller having a control output for starting image data acquisition by said medical imaging apparatus at a time interval $\Delta tm$ after receiving said status signal, with $\Delta tm$ being determined dependent on said time interval $\Delta ti$.

11. A medical imaging apparatus as claimed in claim 10 wherein said first contrast agent bolus has a circulation time in said examination subject associated therewith, and wherein said controller injects said second contrast agent at said predetermined time interval $\Delta ti$ which is less than said circulation time.

12. The improvement of claim 11 further comprising a message output at said controller activated at a predetermined amount of time subsequent to reception of said status signal, but before an end of said time interval $\Delta tm$.

13. The improvement of claim 11 wherein said controller includes means for adjusting a volume of each of said first bolus and said second bolus infused by said first infusion pump.

* * * * *